United States Patent
Kishi

(10) Patent No.: US 9,283,679 B2
(45) Date of Patent: Mar. 15, 2016

(54) MASTER-SLAVE MANIPULATOR AND MEDICAL MASTER-SLAVE MANIPULATOR

(75) Inventor: Kosuke Kishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/353,396

(22) Filed: Jan. 19, 2012

(65) Prior Publication Data
US 2012/0191247 A1    Jul. 26, 2012

(30) Foreign Application Priority Data

Jan. 20, 2011    (JP) ................. 2011-010001

(51) Int. Cl.
| | |
|---|---|
| G05B 15/00 | (2006.01) |
| G05B 19/00 | (2006.01) |
| B25J 9/16 | (2006.01) |
| A61B 19/00 | (2006.01) |
| B25J 3/04 | (2006.01) |

(52) U.S. Cl.
CPC ............ *B25J 9/1689* (2013.01); *A61B 19/2203* (2013.01); *B25J 3/04* (2013.01); *A61B 2019/2223* (2013.01); *G05B 2219/40182* (2013.01); *G05B 2219/40367* (2013.01)

(58) Field of Classification Search
CPC ...... A62B 19/2203; B25J 9/1689; B25J 3/04; A61B 2019/2223; A61B 2019/40367
USPC ............. 700/3, 245, 258, 264, 253, 259, 262; 901/2; 600/102, 103, 424; 318/568.21, 318/568.11, 566, 567; 606/1, 130, 102; 414/2, 4, 5, 7, 8
See application file for complete search history.

(56) References Cited

U.S. PATENT DOCUMENTS

| | | | | |
|---|---|---|---|---|
| 3,923,166 A | * | 12/1975 | Fletcher et al. | 414/4 |
| 4,604,716 A | * | 8/1986 | Kato et al. | 700/251 |
| 4,837,734 A | * | 6/1989 | Ichikawa et al. | 700/249 |

(Continued)

FOREIGN PATENT DOCUMENTS

| | | |
|---|---|---|
| EP | 0 926 994 B1 | 3/2003 |
| EP | 1 854 418 B1 | 11/2007 |

(Continued)

OTHER PUBLICATIONS

JP201017804A_English_Machine_Translation.*

(Continued)

*Primary Examiner* — Jason Holloway
*Assistant Examiner* — Rachid Bendidi
(74) *Attorney, Agent, or Firm* — Scully, Scott, Murphy & Presser, PC

(57) ABSTRACT

A master-slave manipulator includes a slave manipulator, a master operation input device, and a control unit. The slave manipulator includes joints having multiple degrees of freedom. The master operation input device allows an operator to uniquely input a position and an orientation. The device includes a first operation unit configured to output the position and orientation, and a second operation unit including at least a joint configured to output value of the joint independently with the output of the first operation unit. The control unit calculates a driving amount of each joint of the slave manipulator using the position and orientation of the second operation unit and controls the slave manipulator in accordance with a joint driving command value.

6 Claims, 17 Drawing Sheets

(56) References Cited

U.S. PATENT DOCUMENTS

| | | | |
|---|---|---|---|
| 4,887,222 A * | 12/1989 | Miyake et al. | 700/262 |
| 5,943,914 A * | 8/1999 | Morimoto et al. | 74/479.01 |
| 6,280,425 B1 | 8/2001 | Del Guercio | |
| 6,364,888 B1 * | 4/2002 | Niemeyer et al. | 606/130 |
| 6,459,926 B1 * | 10/2002 | Nowlin et al. | 600/429 |
| 6,635,071 B2 | 10/2003 | Boche et al. | |
| 6,659,939 B2 * | 12/2003 | Moll et al. | 600/102 |
| 6,837,883 B2 * | 1/2005 | Moll et al. | 606/1 |
| 6,889,116 B2 | 5/2005 | Jinno | |
| 7,043,338 B2 | 5/2006 | Jinno | |
| 7,454,268 B2 | 11/2008 | Jinno | |
| 7,736,356 B2 | 6/2010 | Cooper et al. | |
| 7,778,733 B2 * | 8/2010 | Nowlin et al. | 700/260 |
| 7,806,891 B2 * | 10/2010 | Nowlin et al. | 606/1 |
| 7,865,266 B2 * | 1/2011 | Moll et al. | 700/245 |
| 7,899,578 B2 * | 3/2011 | Prisco et al. | 700/254 |
| 8,002,784 B2 | 8/2011 | Jinno | |
| 2003/0060927 A1 * | 3/2003 | Gerbi et al. | 700/245 |
| 2007/0288044 A1 | 12/2007 | Jinno et al. | |
| 2008/0154246 A1 * | 6/2008 | Nowlin et al. | 606/1 |
| 2008/0221732 A1 * | 9/2008 | Toth et al. | 700/245 |
| 2008/0232932 A1 | 9/2008 | Jinno | |
| 2009/0088774 A1 * | 4/2009 | Swarup et al. | 606/130 |
| 2009/0099692 A1 * | 4/2009 | Prisco et al. | 700/254 |
| 2010/0198402 A1 * | 8/2010 | Greer et al. | 700/247 |
| 2010/0317965 A1 * | 12/2010 | Itkowitz et al. | 600/425 |
| 2011/0301754 A1 * | 12/2011 | Toth et al. | 700/245 |
| 2012/0078053 A1 * | 3/2012 | Phee et al. | 600/139 |
| 2012/0083801 A1 * | 4/2012 | Nixon | 606/130 |

FOREIGN PATENT DOCUMENTS

| | | |
|---|---|---|
| JP | 63-267177 A | 11/1988 |
| JP | S64-20983 A | 1/1989 |
| JP | H2-198778 A | 8/1990 |
| JP | 4-45313 B2 | 7/1992 |
| JP | 05-228854 | 9/1993 |
| JP | 7-246578 A | 9/1995 |
| JP | 7-276265 A | 10/1995 |
| JP | 2001-501125 A | 1/2001 |
| JP | 2002-102248 A | 4/2002 |
| JP | 2002-128000 A | 5/2002 |
| JP | 2002-172581 A | 6/2002 |
| JP | 2003-340752 | 12/2003 |
| JP | 2003-340752 A | 12/2003 |
| JP | 2005-103741 | 4/2005 |
| JP | 2006-334695 | 12/2006 |
| JP | 2007-301692 A | 11/2007 |
| JP | 2007-325936 A | 12/2007 |
| JP | 2007-535989 A | 12/2007 |
| JP | 2010-17804 A | 1/2010 |
| JP | 2010-29507 A | 2/2010 |
| WO | WO 99/04702 A1 | 2/1999 |
| WO | WO 00/60421 A2 | 10/2000 |
| WO | WO 2009007347 A2 * | 1/2009 |

OTHER PUBLICATIONS

English translation of International Search Report PCT/JP2012/050828 dated Apr. 17, 2012.

English language abstract of Japanese Patent Application No. JP 1016389 A.

Japanese Office Action dated Jul. 15, 2014 from related Japanese Patent Application No. 2011-010001, together with an English language translation.

Jonghyun Choi, et al., "Design and characteristic analysis of 7-DOF hybrid master arm with human arm kinematics", Proceedings of the Asme Dynamic Systems and Control Division, 1998, vol. 64, Dec. 31, 1998, pp. 195-205.

Extended Supplementary European Search Report dated Feb. 20, 2014 in corresponding European Patent Application No. 12737160.7.

Chinese Office Action dated Jul. 3, 2015 from related Chinese Patent Application No. 201280005866.0.

* cited by examiner

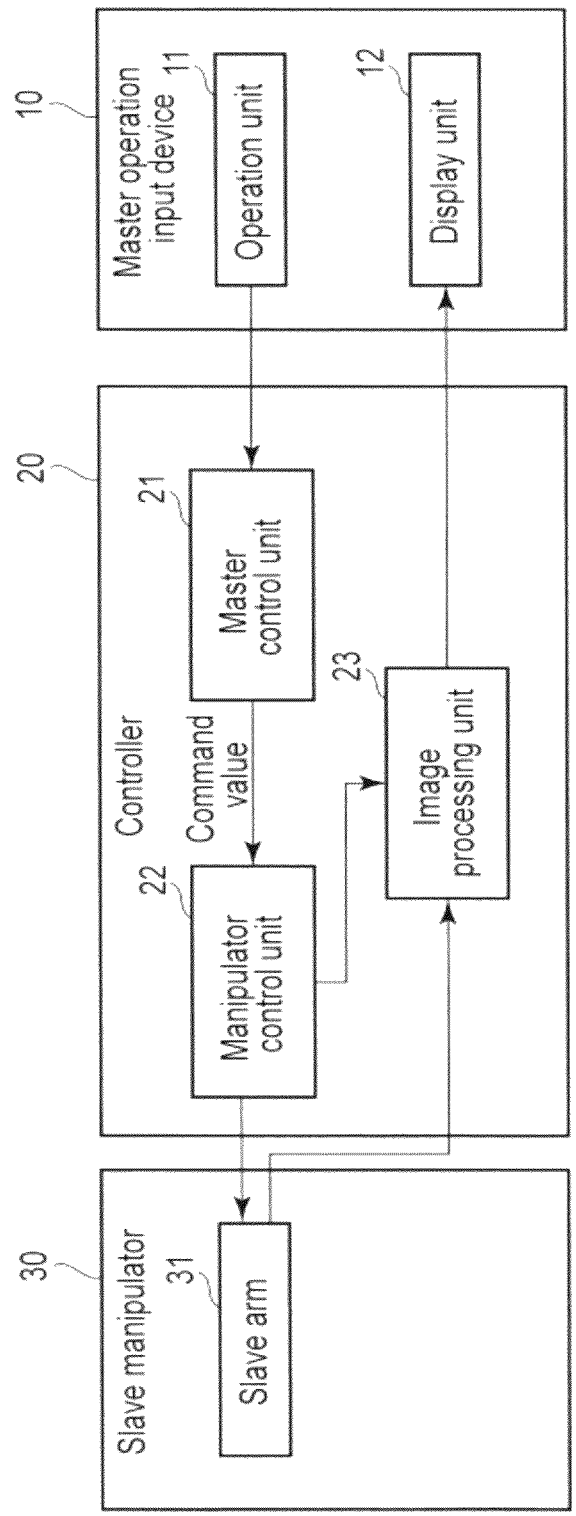
F I G. 1

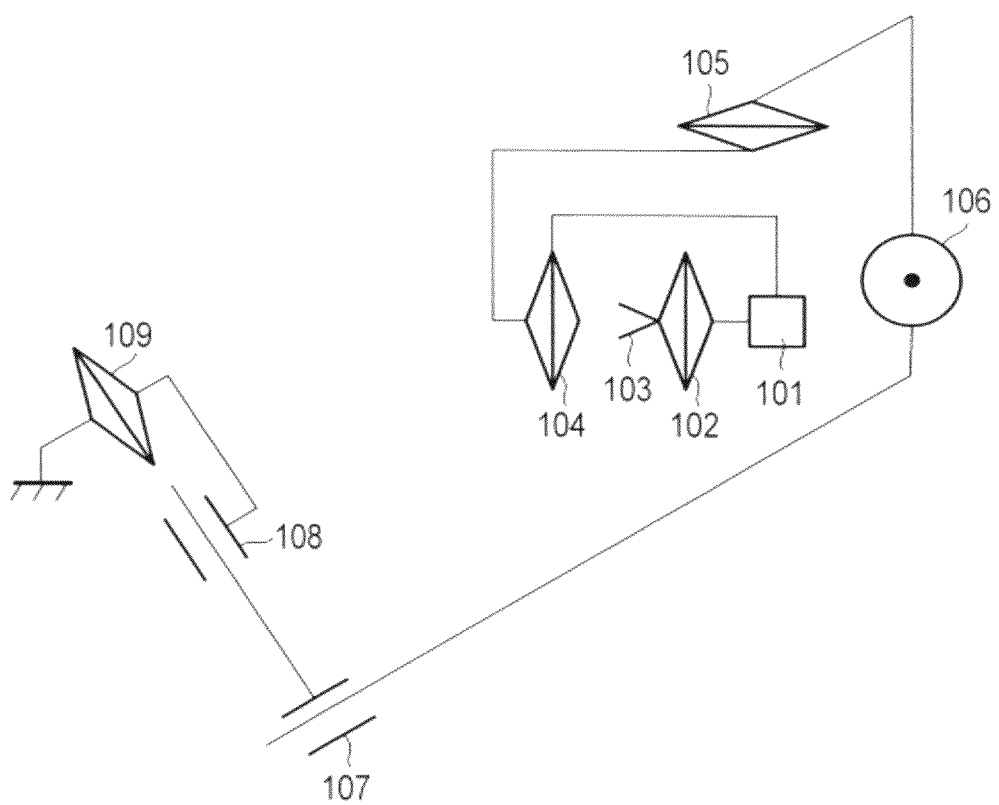
F I G. 2

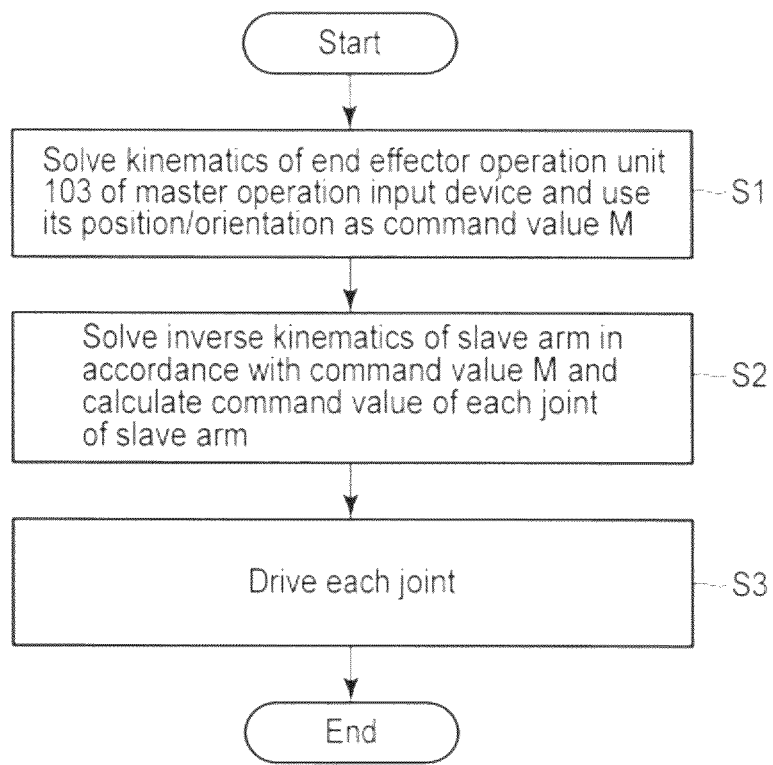
F I G. 4

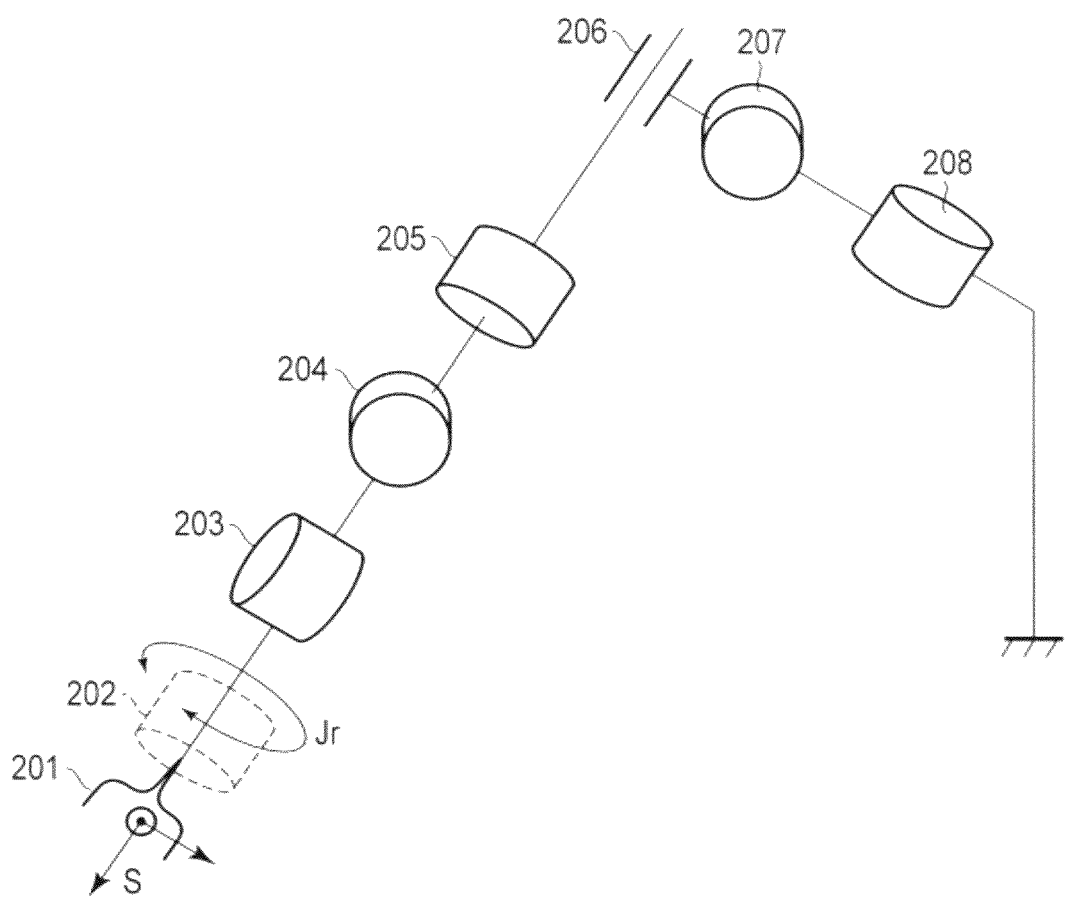
F I G. 7

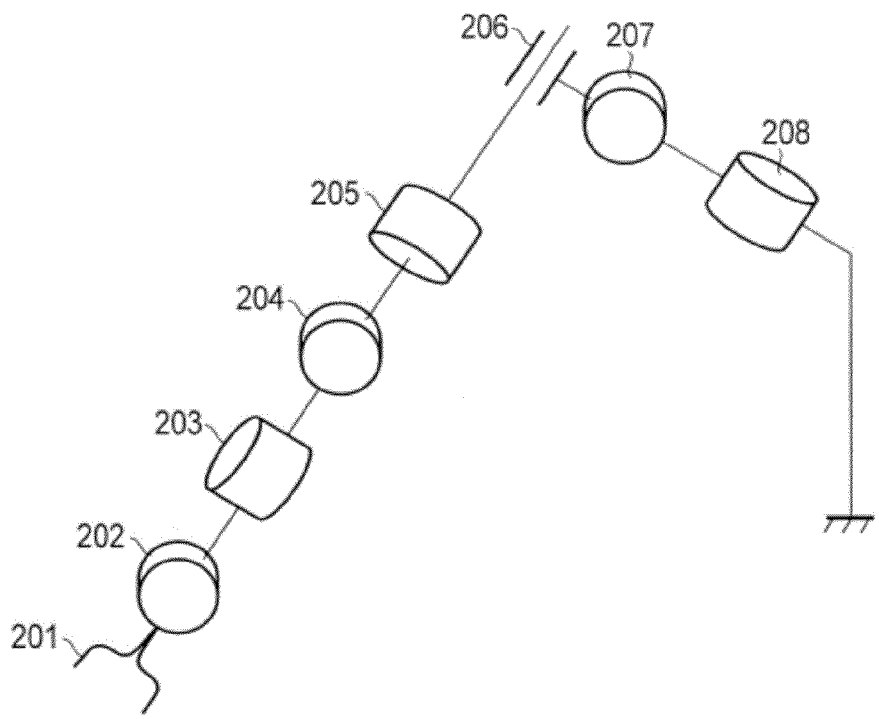
F I G. 10A
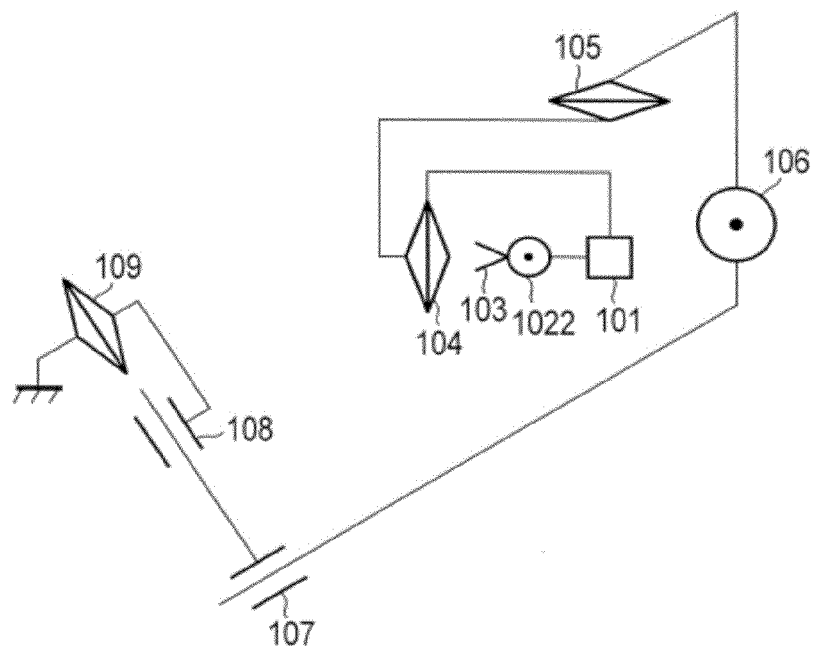
F I G. 10B

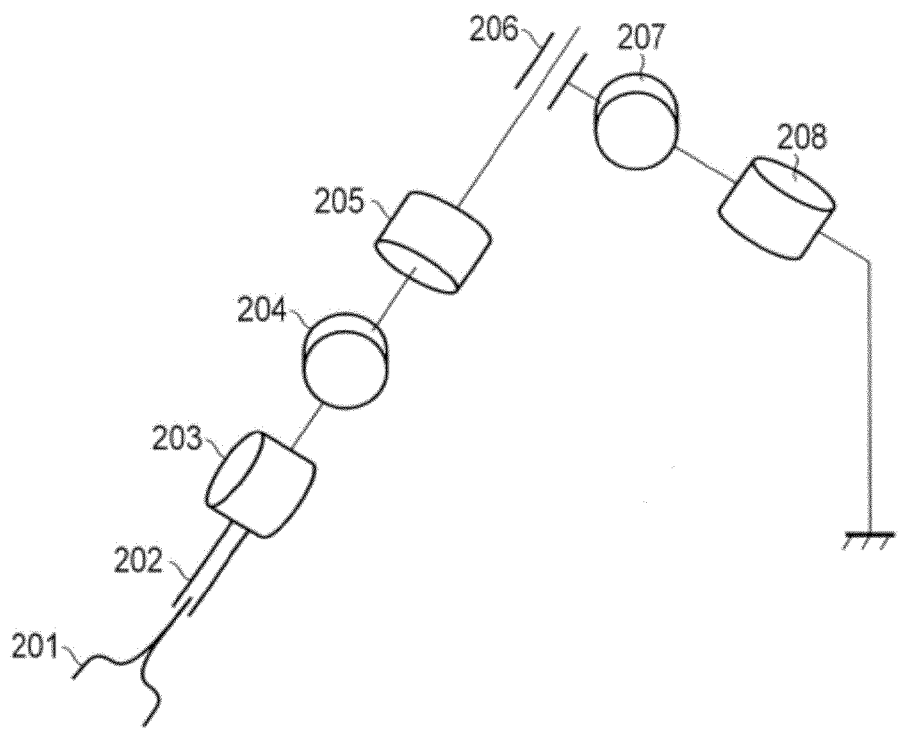
F I G. 11A
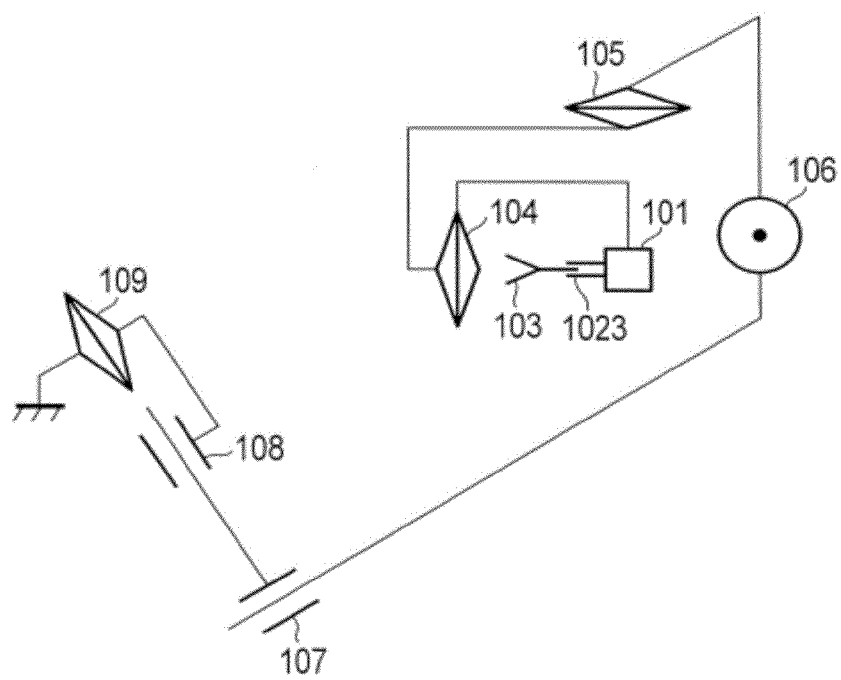
F I G. 11B

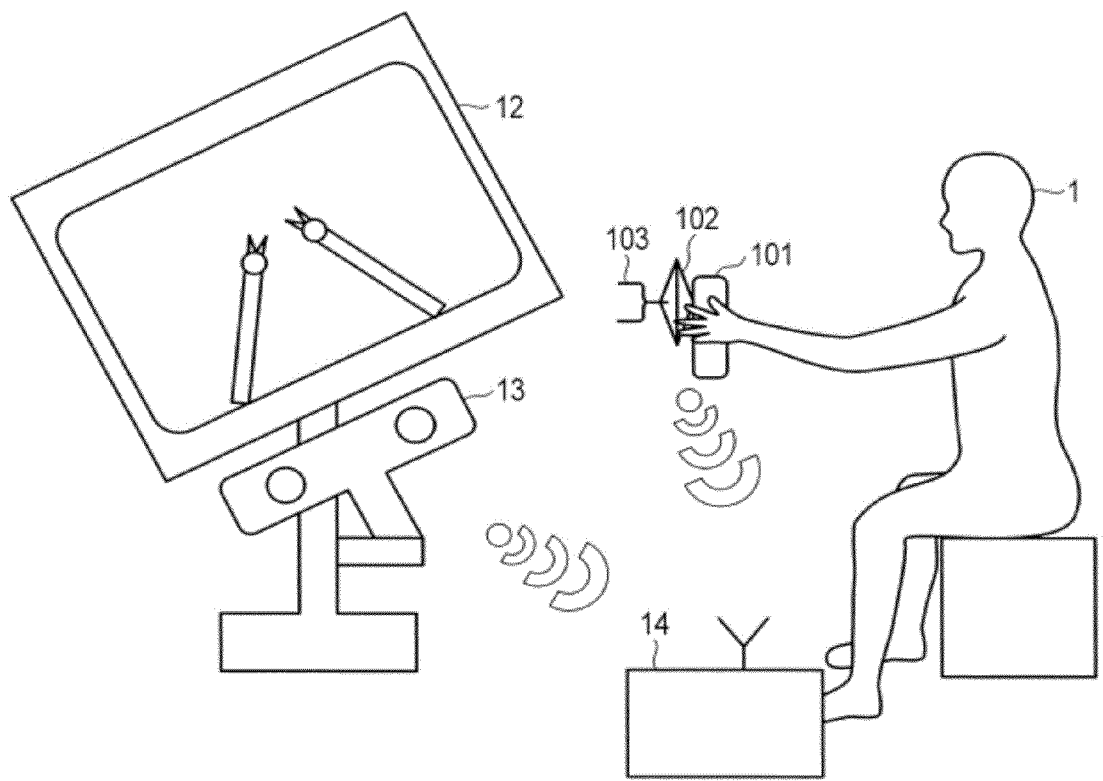
F I G. 13

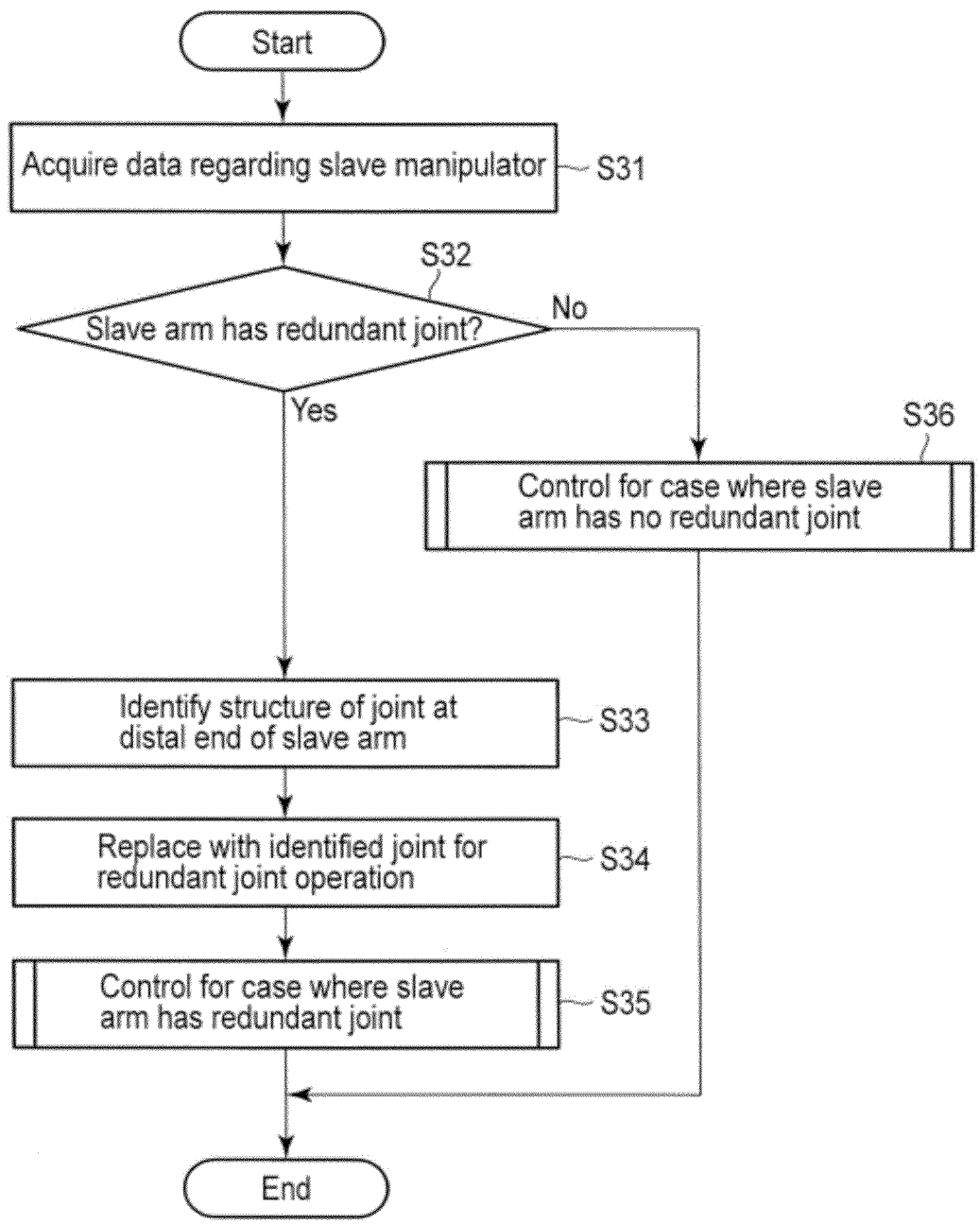
F I G. 18

MASTER-SLAVE MANIPULATOR AND MEDICAL MASTER-SLAVE MANIPULATOR

CROSS-REFERENCE TO RELATED APPLICATIONS

This application is based upon and claims the benefit of priority from prior Japanese Patent Application No. 2011-010001, filed Jan. 20, 2011, the entire contents of which are incorporated herein by reference.

BACKGROUND OF THE INVENTION

1. Field of the Invention

The present invention relates to a master-slave manipulator and a medical master-slave manipulator.

2. Description of the Related Art

Recently, in order to reduce manpower in medical facilities, medical procedures using robots have been under study. Particularly in the field of surgery, various suggestions have been made regarding manipulator systems that use a manipulator having a multidegree-of-freedom (multiarticular) arm to treat a patient. In connection with such manipulator systems, there is known a manipulator system (master-slave manipulator) in which a manipulator (slave manipulator) that comes into direct contact with a body cavity of a patient can be remotely operated by a master operation input device. Recently, there has also come to be known a master-slave manipulator in which a slave arm of a slave manipulator has redundant degrees of freedom. Moreover, there is also known a master-slave manipulator in which an operation unit for operation input to the above-mentioned slave manipulator having redundant degrees of freedom is provided on the side of a master operation input device. For example, according to Jpn. Pat. Appln. KOKAI Publication No. 2006-334695, an arm body configured to transmit the motion of the arm of a user to a slave arm comprises an elbow switch. This elbow switch is provided in a part of the arm body where the elbow of the user is mounted, and is capable of controlling movement having two degrees of freedom.

BRIEF SUMMARY OF THE INVENTION

According to a first aspect of the invention, there is provided a master-slave manipulator comprising: a slave manipulator with joints having multiple degrees of freedom; a master operation input device which allows an operator to uniquely input a position and an orientation, comprising (1) a first operation unit configured to output the position and orientation, and (2) a second operation unit including at least a joint configured to output value of the joint independently with the output of the first operation unit; and a control unit configured to calculate a driving amount of each joint of the slave manipulator using the position and orientation of the second operation unit as a position/orientation input command value for the end of the slave manipulator, to generate a joint driving command value based on the position/orientation input command value, and to control the slave manipulator in accordance with the joint driving command value.

According to a second aspect of the invention, there is provided a master-slave manipulator comprising: a slave manipulator with joints including multiple degrees of freedom; a master operation input device which allows an operator to uniquely input a position and an orientation, comprising (1) a first operation unit configured to output the position and orientation, and (2) a second operation unit including at least a joint configured to output value of the joint independently with the output of the first operation unit; and a control unit (1) configured to calculate a first driving amount of each joint of the slave manipulator by using the position and orientation of the second operation unit as a position/orientation input command value for the end of the slave manipulator, to generate a first joint driving command value based on the first driving amount, and to control the slave manipulator in accordance with the first joint driving command value, when the slave manipulator includes no redundant joint, and (2) configured to calculate a second driving amount of each joint of the slave manipulator by hypothetically using the position and orientation of the first operation unit as a position/orientation input command value for the end of the slave manipulator including no redundant joint on the assumption that the distal end of the redundant joint is a fixed joint, to generate a second joint driving command value including a driving amount of the joint of the second operation unit and the second joint driving amount, and to control the slave manipulator in accordance with the second joint driving command value, when the slave manipulator includes at least a redundant joint.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing the overall configuration of an example of a master-slave manipulator according to embodiments of the present invention;

FIG. 2 is a schematic diagram showing the configuration of an example of an operation unit according to the first embodiment of the present invention;

FIG. 4 is a flowchart showing the operation of a controller of the master-slave manipulator according to the first embodiment of the present invention in which the slave arm has no redundant joint;

FIG. 7 is a schematic diagram of a slave arm assumed in inverse-kinematic computation according to the embodiment in which the slave arm has a redundant joint;

FIG. 10A is a diagram showing the structure of the slave arm according to a modification in which a joint provided in the grip portion is a pitch joint;

FIG. 10B is a diagram showing the structure of the master operation input device according to the modification in which the joint provided in the grip portion is a pitch joint;

FIG. 11A is a diagram showing the structure of the slave arm according to a modification in which a joint provided in the grip portion is a translation joint;

FIG. 11B is a diagram showing the structure of the master operation input device according to the modification in which the joint provided in the grip portion is a translation joint;

FIG. 13 is a diagram showing an example of a wireless operation unit;

FIG. 18 is a flowchart illustrating the operation of a master-slave manipulator according to the third embodiment of the present invention.

DETAILED DESCRIPTION OF THE INVENTION

Figure 3A:
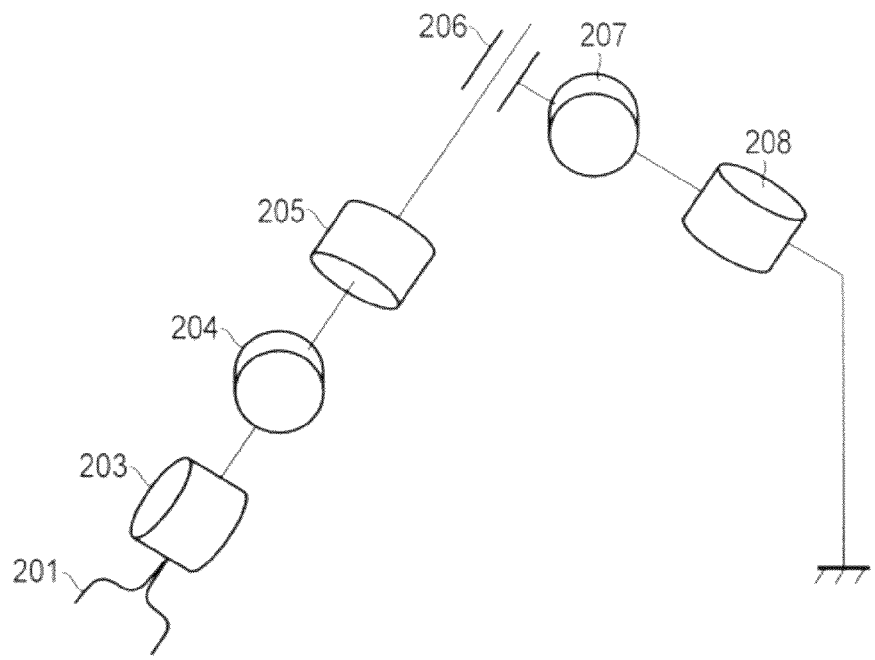
FIG. 3A is a diagram showing an example of the structure of a slave arm having no redundant joint.

Embodiments according to the present invention will hereinafter be described with reference to the drawings.

[First Embodiment]

The first embodiment of the present invention is described. FIG. 1 is a diagram showing the overall configuration of an example of a master-slave manipulator according to embodiments of the present invention. As shown in FIG. 1, the master-slave manipulator according to the embodiments comprises a master operation input device 10, a controller 20, and a slave manipulator 30.

The master operation input device 10 functions as a master in the master-slave manipulator, and comprises, for example, an operation unit 11 and a display unit 12.

The operation unit 11 is fixed to, for example, the display unit 12, and when operated by an operator, outputs an operation signal for operating the slave manipulator 30.

FIG. 2 is a schematic diagram showing the configuration of an example of the operation unit 11 according to the first embodiment of the present invention. The operation unit 11 shown by way of example in FIG. 2 has a grip portion 101. The grip portion 101 is a portion to be gripped by an operator with his/her hand. The grip portion 101 is supported movably in the directions of three orthogonal axes and in the directions to rotate around the respective axes.

A first roll joint 102 as an example of a second operation unit is pivotally fastened to the grip portion 101 as an example of a first operation unit. The first roll joint 102 is based on the grip portion 101, and is operable independently of the grip portion 101. The first roll joint 102 is configured to be able to be rotated by a fingertip when the operator holds the grip portion 101 with his/her hand. An unshown position sensor (e.g., an encoder) is provided in the vicinity of the first roll joint 102. When the first roll joint 102 is rotated by the operator, a resultant driving amount (rotation amount) is detected by the position sensor. From this position sensor, an operation signal corresponding to the driving amount (rotation amount) of the first roll joint 102 is input to a master control unit 21 of the controller 20.

An end effector operation unit 103 is attached to the first roll joint 102. That is, the first roll joint 102 and the end effector operation unit 103 are operably attached independently of the position and orientation of the grip portion 101, and constitute the second operation unit. The end effector operation unit 103 is configured to be able to be opened/closed with a fingertip when the operator holds the grip portion 101 with his/her hand. An unshown position sensor (e.g., an encoder) is provided in the vicinity of the end effector operation unit 103. When the end effector operation unit 103 is opened/closed by the operator, a resultant opening/closing amount (opening/closing angle) is detected by the position sensor. From this position sensor, an operation signal corresponding to the opening/closing amount of the end effector operation unit 103 is input to the master control unit 21 of the controller 20.

The grip portion 101 is attached to a first link. A second roll joint 104 is pivotally fastened to the first link. An unshown position sensor (e.g., an encoder) is provided in the vicinity of the second roll joint 104. When the second roll joint 104 is driven in response to the operation of the grip portion 101 by the operator, a resultant driving amount (rotation amount) is detected by the position sensor. From this position sensor, an operation signal corresponding to the driving amount of the second roll joint 104 is input to the master control unit 21 of the controller 20.

The second roll joint 104 is attached to a second link. A first yaw joint 105 is pivotally fastened to the second link. An unshown position sensor (e.g., an encoder) is provided in the vicinity of the first yaw joint 105. When the first yaw joint 105 is driven in response to the operation of the grip portion 101 by the operator, a resultant driving amount (rotation amount) is detected by the position sensor. From this position sensor, an operation signal corresponding to the driving amount of the first yaw joint 105 is input to the master control unit 21 of the controller 20.

The yaw joint 105 is attached to a third link. A pitch joint 106 is pivotally fastened to the third link. An unshown position sensor (e.g., an encoder) is provided in the vicinity of the pitch joint 106. When the pitch joint 106 is driven in response to the operation of the grip portion 101 by the operator, a resultant driving amount (rotation amount) is detected by the position sensor. From this position sensor, an operation signal corresponding to the driving amount of the pitch joint 106 is input to the master control unit 21 of the controller 20.

The pitch joint 106 is attached to a fourth link. The fourth link is attached to a first translation joint 107. An unshown position sensor (e.g., an encoder) is provided in the vicinity of the first translation joint 107. When the first translation joint 107 is driven in response to the operation of the grip portion 101 by the operator, a resultant driving amount (translation amount) is detected by the position sensor. From this position sensor, an operation signal corresponding to the driving amount of the first translation joint 107 is input to the master control unit 21 of the controller 20.

A fifth link extends from the first translation joint 107. The fifth link is attached to a second translation joint 108. An unshown position sensor (e.g., an encoder) is provided in the vicinity of the second translation joint 108. When the second translation joint 108 is driven in response to the operation of the grip portion 101 by the operator, a resultant driving amount (translation amount) is detected by the position sensor. From this position sensor, an operation signal corresponding to the driving amount of the second translation joint 108 is input to the master control unit 21 of the controller 20.

The second translation joint 108 is attached to a sixth link. A second yaw joint 109 is pivotally fastened to the sixth link. Further, the second yaw joint 109 is fixed to, for example, the display unit via a seventh link. An unshown position sensor (e.g., an encoder) is provided in the vicinity of the second yaw joint 109. When the second yaw joint 109 is driven in response to the operation of the grip portion 101 by the operator, a resultant driving amount (rotation amount) is detected by the position sensor. From this position sensor, an operation signal corresponding to the driving amount of the second yaw joint 109 is input to the master control unit 21 of the controller 20.

According the configuration described above, the operation unit 11 shown in FIG. 2 inputs, to the master control unit 21 of the controller 20, the operation signals (+ the operation signal of the end effector) that correspond to seven degrees of freedom, including six operation signals corresponding to the changes in the position and orientation of the grip portion 101 and the operation signal indicating the operation amount of the first roll joint 102. The operator grips the grip portion 101 in his/her palm, and grips the end effector operation unit 103 with his/her finger. Thus, the operator can move the first roll joint 102 by moving his/her finger relative to his/her palm, and can move the end effector operation unit by moving his/her finger. The position and orientation of the grip portion 101 can be uniquely determined by the six joints 109, 108, 107, 106, 105, and 104. Moreover, the first roll joint 102 can be used to rotate the end effector operation unit 103 independently of the position and orientation of the grip portion 101 and open/close the end effector operation unit 103.

Here, the explanation continues returning to FIG. 1. The display unit 12 shown in FIG. 1 comprises, for example, a liquid crystal display, and displays an image in accordance with an image signal input from the controller 20. As will be described later, the image signal input from the controller 20 is provided by processing, in the controller 20, an image signal which is obtained via an electronic camera (electronic endoscope) attached to the slave arm 31. The image based on such an image signal is displayed on the display unit 12 so that the operator of the master operation input device 10 can check an image of the end of the slave manipulator 30 located apart from the master operation input device 10.

The controller 20 comprises the master control unit 21, a manipulator control unit 22, and an image processing unit 23.

The master control unit 21 calculates command values for the position and orientation of the end of the slave arm 31, for example, by kinematic computation in accordance with the operation signals from the master operation input device 10, and outputs the command values for the position and orientation to the manipulator control unit 22. The master control unit 21 also outputs, to the manipulator control unit 22, the operation signal for giving a command regarding the driving amount of the distal joint and the operation signal for giving a command regarding the driving amount of the end effector from the master operation input device 10.

In response to the command values for the position and orientation from the master control unit 21, the manipulator control unit 22 calculates a command value for the driving amount of each joint of the slave arm 31 necessary for the position and orientation of the end of the slave arm 31 to correspond to the command values. The manipulator control unit 22 then drives each joint of the slave arm 31 in accordance with the calculated command value. A method of calculating the driving amount of each joint will be described later. The manipulator control unit 22 also drives the end effector of the slave arm 31 in response to the operation signal for giving a command regarding the driving amount of the end effector from the master control unit 21.

The image processing unit 23 processes the image signal obtained from the electronic camera (e.g., electronic endoscope) provided at the end of the slave arm 31, and generates an image signal to be displayed on the display unit 12, and then outputs the image signal to the display unit 12.

The slave manipulator 30 has the slave arm 31. Each joint of the slave arm 31 is driven in accordance with a control signal from the manipulator control unit 22. Examples of the structure of the slave arm 31 are shown in FIG. 3A and FIG. 3B.

The slave arm 31 in the example shown in FIG. 3A has no redundant joint. The slave arm 31 has, for example, a series of six joints 203 to 208. An end effector 201 is further attached to joint 203 at the distal end of the slave arm 31. Here, the joint at the distal end means a joint located farthest from the side where the slave arm 31 is fixed. The end effector 201 shown in FIG. 3A is an example of a gripper. Instead, a surgical instrument such as a camera (e.g., electronic endoscope) or an electric scalpel may be attached to the end, and the end is interchangeable.

Among the joints shown in FIG. 3A, joint 205 is a roll joint, joints 203 and 208 are yaw joints, and joints 204 and 207 are pitch joints. Joint 206 is a translation joint. Three degrees of freedom in position and three degrees of freedom in orientation of the end of the slave arm 31 are obtained by driving joints 203 to 208 shown in FIG. 3A in cooperation with one another.

Figure 3B:
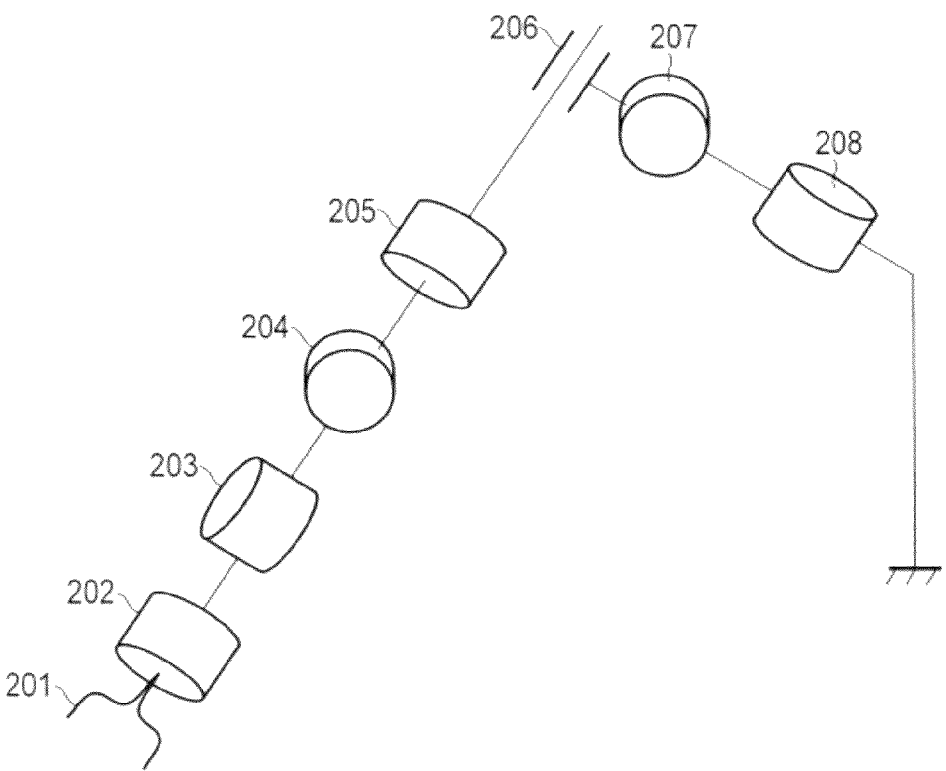
FIG. 3B is a diagram showing an example of the structure of the slave arm having a redundant joint.

The slave arm 31 in the example shown in FIG. 3B has a redundant joint. In this slave arm 31, a roll joint 202 is additionally provided to be coupled to joint 203 of the slave arm 31 shown in FIG. 3A. The end effector 201 is further attached to joint 202. Here, in the present embodiment, the structure of the redundant joint located at the distal end of the slave arm 31 is the same as the structure of joint 102 for redundant joint operation provided in the vicinity of the grip portion 101 of the master operation input device. For example, in the example shown in FIG. 2, joint 102 is a roll joint. In this case, joint 202 is also a roll joint.

Three degrees of freedom in position and three degrees of freedom in orientation of the end of the slave arm 31 are obtained by driving joints 203 to 208 shown in FIG. 3B in cooperation with one another. In addition to these joints, joint 202 for rolling the end effector 201 is provided as the redundant joint in FIG. 3B. Such a configuration makes it possible to, for example, only roll the part in the vicinity of the end effector 201 when rolling the slave arm 31.

As the surgical instrument is interchangeable, the location of the joint at the end of the surgical instrument may be changed during surgery as shown in FIG. 3A and in FIG. 3B in the case of, for example, a medical master-slave manipulator. Moreover, multiple slave manipulators may be switched and operated by one master operation input device. The slave manipulator without redundancy shown in FIG. 3A and the slave manipulator with redundancy shown in FIG. 3B may be switched and operated.

The operation of the master-slave manipulator according to the present embodiment is described below. In the present embodiment, the operation varies depending on whether the slave arm 31 has a redundant joint.

FIG. 4 is a flowchart showing the operation of the controller 20 of the master-slave manipulator according to the present embodiment in which the slave arm 31 has no redundant joint.

The operator who grips the operation unit 11 of the master operation input device 10 operates the operation unit 11 such that the joints constituting the operation unit 11 are driven accordingly. If the joints are driven, their driving amounts are detected by the unshown position sensors, and operation signals are input to the controller 20 from the position sensors.

Figure 5A:
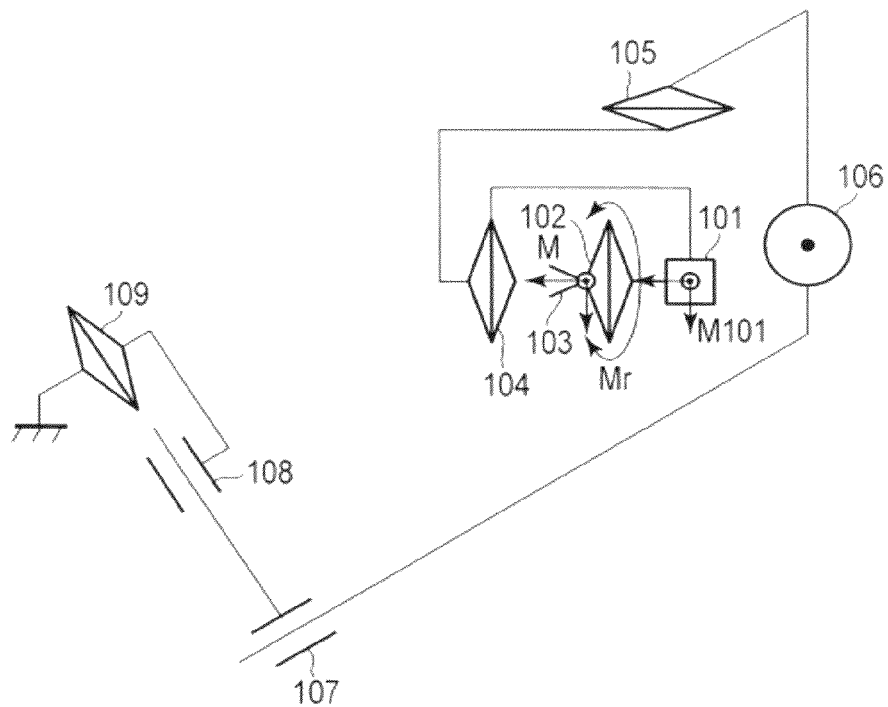
FIG. 5A is a schematic diagram of a master operation input device.
Figure 5B:
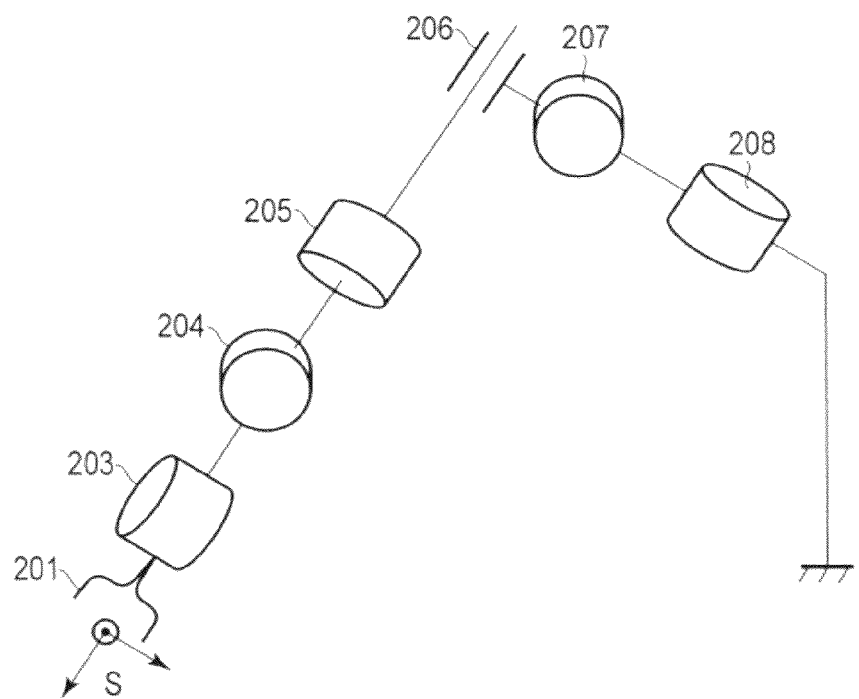
FIG. 5B is a schematic diagram of a slave arm assumed in inverse-kinematic computation according to the embodiment in which the slave arm has no redundant joint.

A case where the slave arm 31 has no redundant joint is described with reference to FIG. 5A and FIG. 5B. FIG. 5A is a schematic diagram of the master operation input device. When the slave arm 31 has no redundant joint, the master control unit 21 of the controller 20 solves kinematics in accordance with the operation signals input from the operation unit 11 to find a position/orientation M of the end effector operation unit 103 of the master operation input device 10 as command values for the position and orientation of the end of the slave arm 31. The position and orientation of the end effector operation unit 103 can be calculated by computing kinematics from joints 109, 108, 107, 106, 105, 104, and 102 and the lengths of the links that connect these joints. Actually, the operator operates the grip portion 101 in his/her palm, so that the operation amount of the first roll joint 102 can be added to a position/orientation M101 of the grip portion 101 to compute the position/orientation M of the end effector operation unit 103. The master control unit 21 then inputs the calculated command value M to the manipulator control unit 22 (step S1).

Furthermore, the manipulator control unit 22 solves the inverse kinematics of the end of the slave arm 31 in accordance with the input command value M to find command values regarding the driving amounts of the joints of the slave arm 31 (step S2). FIG. 5B is a schematic diagram of the slave arm 31 assumed in the inverse-kinematic computation according to the present embodiment in which the slave arm 31 has no redundant joint. When the slave arm 31 has no redundant joint, the inverse kinematics is solved for the end position in FIG. 5B. When the slave arm 31 has no redundant joint, the inverse kinematics can be relatively easily solved.

After finding the command values regarding the driving amounts of the joints, the manipulator control unit 22 inputs the found command values to the slave manipulator 30, and drives the joints of the slave arm 31 (step S3).

Figure 6:
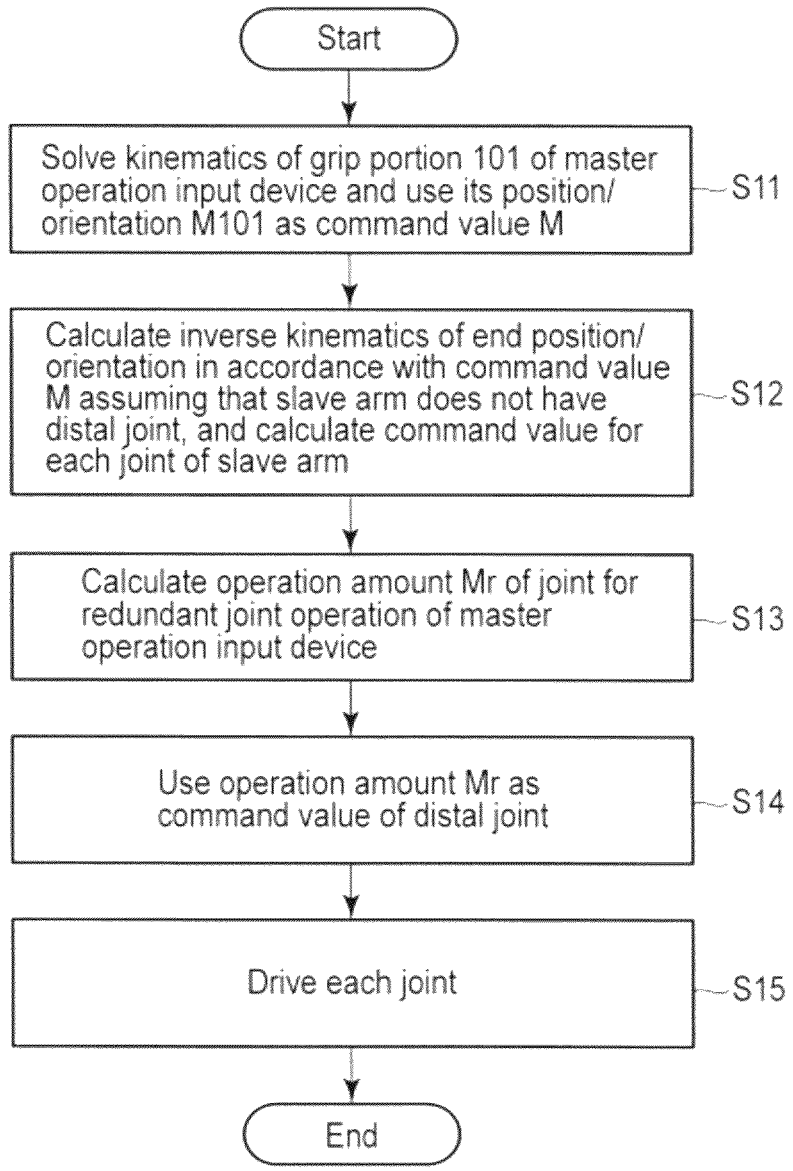
FIG. 6 is a flowchart showing the operation of the controller of the master-slave manipulator according to the first embodiment of the present invention in which the slave arm has a redundant joint.

FIG. 6 is a flowchart showing the operation of the controller 20 of the master-slave manipulator according to the present embodiment in which the slave arm 31 has a redundant joint.

When the slave arm 31 has a redundant joint, the master control unit 21 of the controller 20 solves the kinematics of the grip portion 101 of the master operation input device 10 in accordance with the operation signals corresponding to joints 104 to 109 input from the operation unit 11 to find the position/orientation M101 of the grip portion 101 as the command value M for the position and orientation of the end of the slave arm 31. The master control unit 21 then inputs the calculated command value M to the manipulator control unit 22 (step S11).

Furthermore, the manipulator control unit 22 solves the inverse kinematics of the end of the slave arm 31 in accordance with the input command value M on the assumption that the slave arm 31 does not have joint 202 (i.e., on the assumption that joint 202 is a fixed joint), and thereby finds command values regarding the driving amounts of joints 203 to 208 of the slave arm 31 (step S12). FIG. 7 is a schematic diagram of the slave arm 31 assumed in the inverse-kinematic computation according to the present embodiment in which the slave arm 31 has a redundant joint. In the present embodiment, the first roll joint 102 and joint 202 have the same structure, and a command can be directly given by the first roll joint regarding the driving amount of joint 202. Therefore, when the slave arm 31 has a redundant joint as shown in FIG. 7, the position and orientation of the end of the slave arm 31 can be correctly controlled even if the inverse kinematics is solved on the assumption that the slave arm 31 has no redundant joint. The inverse kinematics is solved on the assumption that the slave arm 31 does not have joint 202 at the end, such that the inverse kinematics can be relatively easily solved without performing a redundant inverse-kinematic computation.

The master control unit 21 then finds an operation amount (rotation amount of the first roll joint 102 shown in FIG. 5A) Mr of the first roll joint 102 in accordance with the operation signal corresponding to the first roll joint 102 input from the operation unit 11, and inputs the found operation amount Mr to the manipulator control unit 22 (step S13). Accordingly, the manipulator control unit 22 uses the operation amount Mr as the driving amount (rotation amount of joint 202 shown in FIG. 7) of joint 202 at the distal end of the slave arm 31 (step S14).

After finding the command values regarding the driving amounts of the joints, the manipulator control unit 22 inputs the found command values to the slave manipulator 30, and drives the joints of the slave arm (step S15).

As described above, in the present embodiment, the operation unit 11 of the master operation input device 10 has a first roll joint 102 which serves as an operable joint for the operator to give a command regarding the driving amount of the redundant joint of the slave arm 31. When the slave arm 31 has no redundant joint, the inverse kinematics of the whole slave arm 31 is solved to find the driving amounts of the joints. When the slave arm 31 has a redundant joint, the driving amounts of the joints other than redundant joint 202 are found by solving the inverse kinematics on the assumption that the slave arm 31 does not have joint 202 at the distal end. The driving amount of the redundant joint 202 is found by using the command values from the master operation input device 10. Thus, in the present embodiment, load on the inverse-kinematic computation can be reduced regardless of whether or not the slave arm 31 has a redundant joint. Consequently, the same master operation input device can be used for master-slave operation even if the joint structure of the slave manipulator is modified.

The case where the slave arm 31 has a redundant joint and the case where the slave arm 31 has no redundant joint are separately described above. However, whether the slave arm 31 has the redundant joint is repetitively determined from time to time as shown in FIG. 8, so that joint driving command values for the slave manipulator can be modified in real time during surgery by the control unit even if the joint configuration of the end effector of the slave arm 31 is modified during the master-slave operation.

Figure 8:
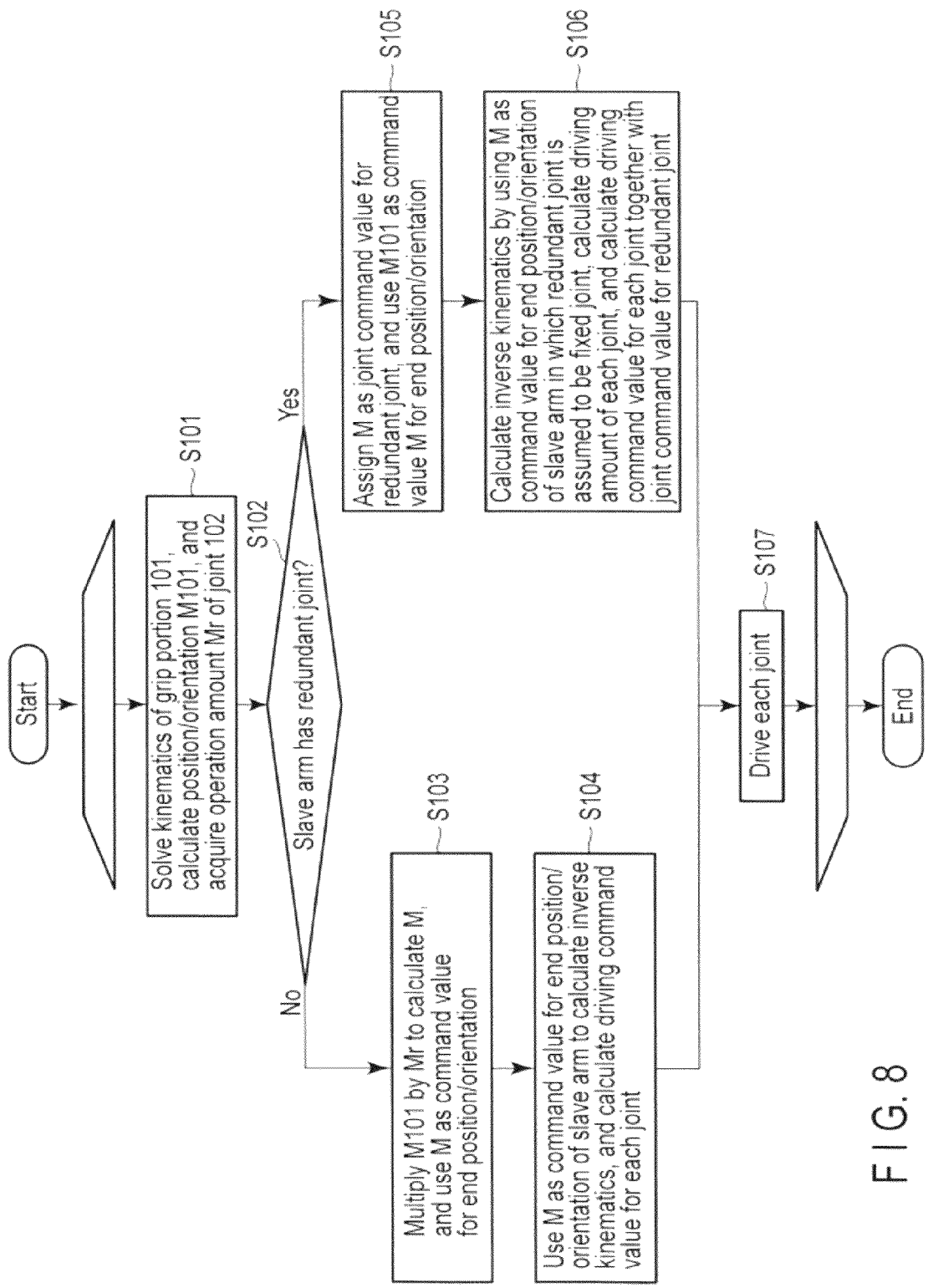
FIG. 8 is a flowchart showing the operation of the controller which makes a switch (determination) as to whether the slave arm has a redundant joint or not.

In FIG. 8, the master control unit 21 of the controller 20 solves the kinematics to calculate the position/orientation M101 of the grip portion 101 of the master operation input device 10 in accordance with the operation signals input from the operation unit 11. The master control unit 21 also acquires the operation amount Mr of the first roll joint 102 from the operation signal of joint 102 input from the operation unit 11 (step S101).

The master control unit 21 then determines whether the slave arm 31 of the slave manipulator 30 has a redundant joint (step S102). As a component for this determination, the master control unit 21 has a memory therein. A flag for recognizing whether the slave arm 31 has a redundant joint is stored in the memory. For example, a flag "1" is stored in the memory when the slave arm 31 has a redundant joint, and a flag "0" is stored in the memory when the slave arm 31 has no redundant joint. The master control unit 21 performs the determination in step S102 by reading the flag from the memory.

When determining in step S102 that the slave arm 31 has no redundant joint, the master control unit 21 multiplies the position/orientation M101 of the grip portion 101 calculated in step S101 by the operation amount Mr of joint 102, and thereby calculates the command value M for the position and orientation of the end of the slave arm 31 (step S103).

The manipulator control unit 22 solves the inverse kinematics of the end of the slave arm 31 in accordance with the command value M calculated by the master control unit 21 in step S103 to find command values regarding the driving amounts of the joints of the slave arm 31 (step S104).

When determining in step S102 that the slave arm 31 has a redundant joint, the master control unit 21 of the controller 20 uses the operation amount Mr of joint 102 input from the operation unit 11 as the driving amount of joint 202, and uses the position/orientation M101 as the command value M for the position and orientation of the end of the slave arm 31 (step S105).

The manipulator control unit 22 solves the inverse kinematics of the end of the slave arm 31 in accordance with the input command value M on the assumption that the slave arm 31 does not have joint 202 (on the assumption that joint 202 is a fixed joint), and thereby finds command values regarding the driving amounts of joints 203 to 208 of the slave arm 31. The manipulator control unit 22 also uses the operation amount Mr as the driving amount of joint 202 at the distal end of the slave arm 31 (step S106).

After finding the command values regarding the driving amounts of the joints, the manipulator control unit 22 inputs the found command values to the slave manipulator 30, and drives the joints of the slave arm 31 (step S107). The above-described control shown in FIG. 8 is repeated from time to time.

[Modifications]

Figure 9A:
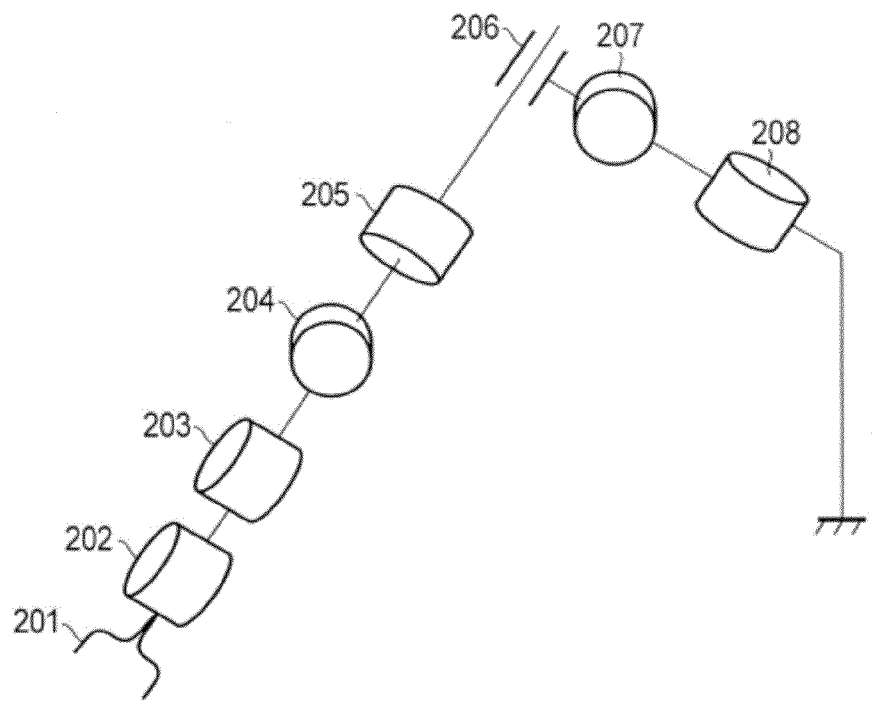
FIG. 9A is a diagram showing the structure of the slave arm according to a modification in which a joint provided in the grip portion is a yaw joint.
Figure 9B:
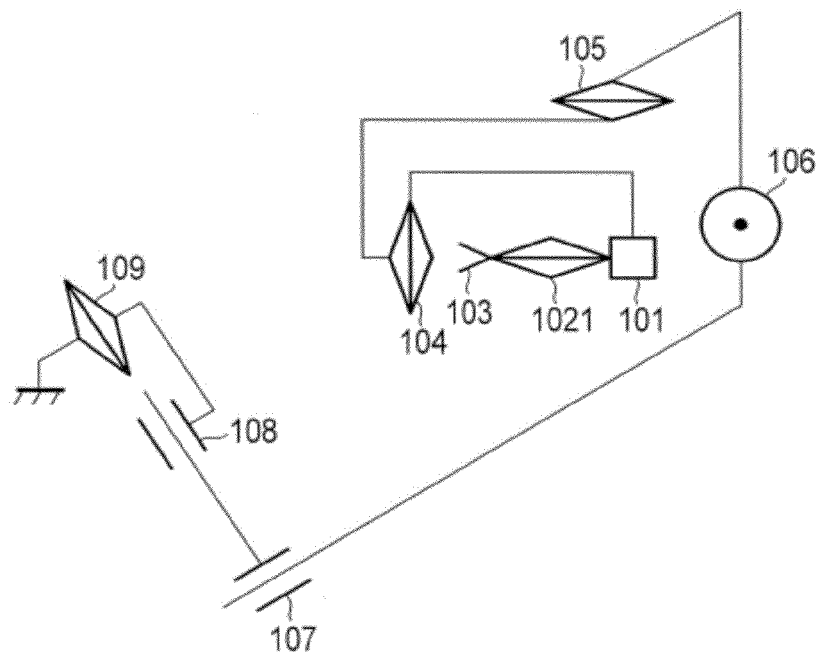
FIG. 9B is a diagram showing the structure of the master operation input device according to the modification in which the joint provided in the grip portion is a yaw joint.

Modifications of the embodiment are described below. In the example shown in FIG. 2, the roll joint is provided in the grip portion 101. This is attributed to the fact that the joint at the distal end (the end effector) of the slave arm 31 is a roll joint. When the joint at the distal end of the slave arm 31 is not a roll joint, the joint provided in the grip portion 101 is also changed. For example, when the joint at the distal end of the slave arm 31 is a yaw joint as shown in FIG. 9A, a joint 1021 provided in the grip portion 101 is also a yaw joint as shown in FIG. 9B. Similarly, when the joint at the distal end of the slave arm 31 is a pitch joint as shown in FIG. 10A, a joint 1022 provided in the grip portion 101 is also a pitch joint as shown in FIG. 10B. When the joint at the distal end of the slave arm 31 is a translation joint as shown in FIG. 11A, a joint 1023 provided in the grip portion 101 is also a translation joint as shown in FIG. 11B.

Figure 12A:
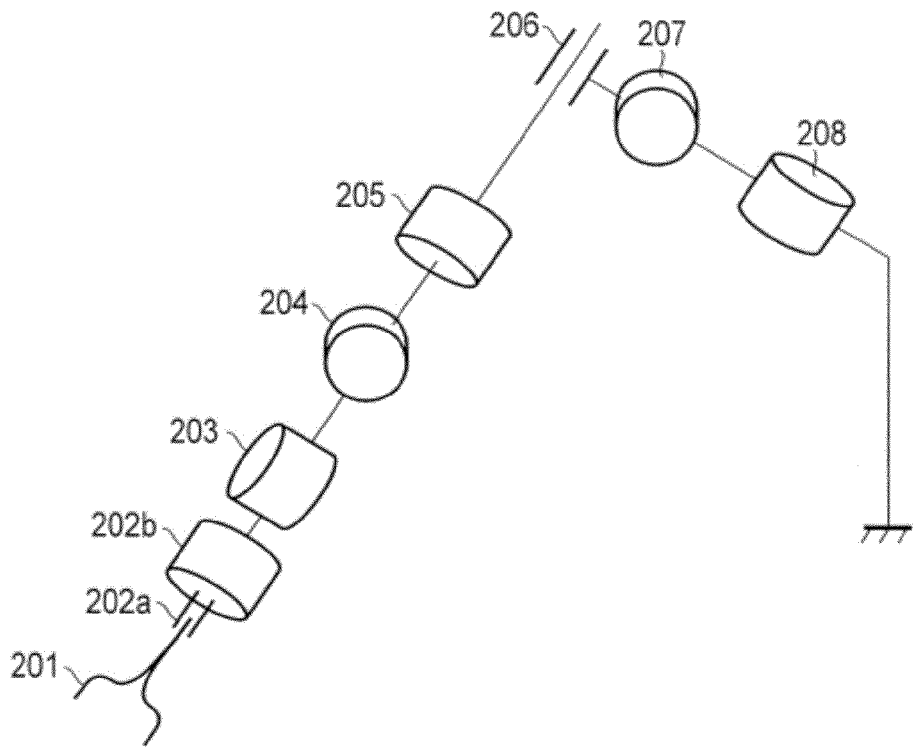
FIG. 12A is a diagram showing the structure of the slave arm according to a modification in which multiple joints are provided in the grip portion.
Figure 12B:
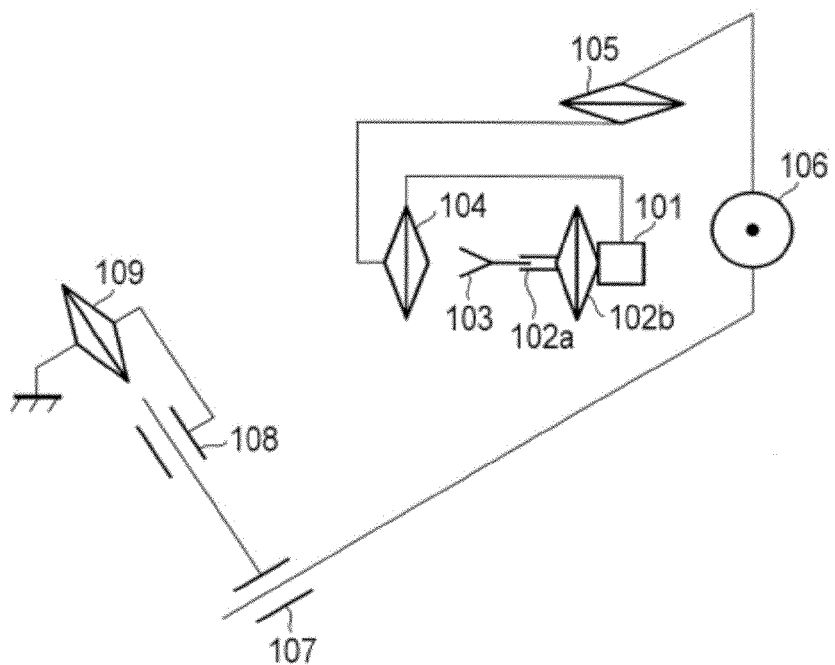
FIG. 12B is a diagram showing the structure of the master operation input device according to the modification in which the multiple joints are provided in the grip portion.

Moreover, when two or more kinds of independent joints 202a and 202b are provided at the distal end of the slave arm 31 as shown in FIG. 12A, more than one joint are provided in the grip portion 101. For example, FIG. 12A shows the slave arm 31 having eight degrees of freedom in which the roll joint 202b and the translation joint 202a are added to joints 203 to 208 corresponding to six degrees of freedom. In this case, the grip portion 101 is also provided with two joints including a roll joint 102b and a translation joint 102a that can be independently operated. Such a configuration allows the joint at the distal end of the slave arm 31 to have the same structure as the joint provided in the grip portion 101. This enables the operator to intuitively operate the roll joint 202b and the translation joint 202a of the slave arm 31. Two joints are provided in the example shown in FIG. 12B. However, when the number of joints of the slave arm 31 is increased, the number of joints provided in the grip portion 101 of the master operation input device 10 is also increased accordingly.

When the structure of the end effector 201 of the slave arm 31 is different from the structure shown in FIG. 3, it is preferable to also change the structure of the end effector operation unit 103 accordingly.

Furthermore, joints 104 to 109 provided in the operation unit 11 shown in FIG. 2 serve to give commands regarding the position and orientation of the end of the slave arm 31. Joints 104 to 109 may not be used as long as commands can be given regarding the position and orientation of the end of the slave arm 31. For example, if a sensor (e.g., an acceleration sensor) for detecting the translation of three axes is provided in the operation unit 11, the operation unit 11 can be configured as shown in FIG. 13. In the example shown in FIG. 13, if an operator 1 grips the grip portion 101 of the operation unit 11 to move or rotate the operation unit 11 in a three-dimensional space, operation signals corresponding to three degrees of freedom in position can be given. Operation signals corresponding to three degrees of freedom in orientation are obtained by analyzing the image obtained, for example, by a camera 13. FIG. 13 shows an example wherein the operation signal obtained by the operation unit 11 can be wirelessly communicated via a wireless communication unit 14. It should be understood that the operation signal obtained by the operation unit 11 may be communicated in a wired manner in the example shown in FIG. 13. It should also be understood that the orientation of the operation unit 11 may be detected by an angular velocity sensor.

Figure 14:
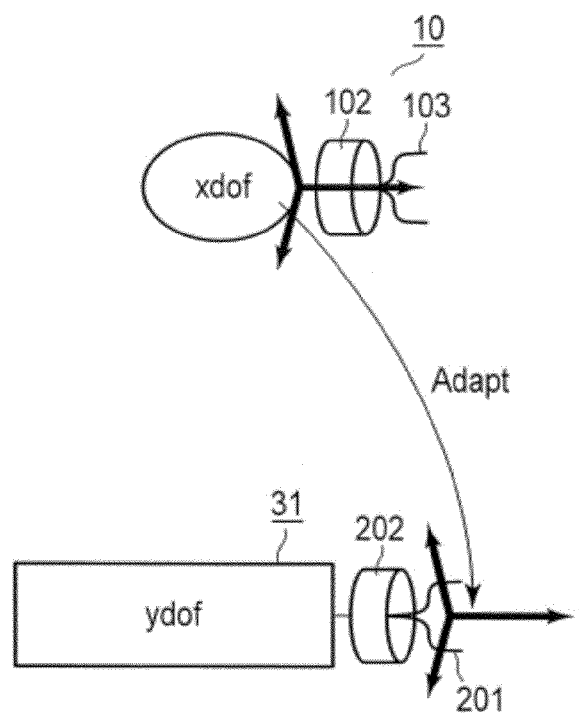
FIG. 14 is a diagram showing an example in which the structure is varied except for a distal end.

As described above, as long as joint 102 for redundant joint operation in the master operation input device 10 has the same structure as the redundant joint 202 at the distal end of the slave arm 31, the technique according to the present embodiment can be applied even if the structure is different in other parts. That is, the technique according to the present embodiment can be applied as long as joint 102 has the same structure as joint 202 even if the master operation input device 10 has a given structure that uses some part other than joint 102 to give command values for x degrees of freedom (DOF) and the slave arm 31 has a given structure that uses some part other than joint 202 to enable driving having y degrees of freedom as shown in FIG. 14.

[Second Embodiment]

Figure 15:
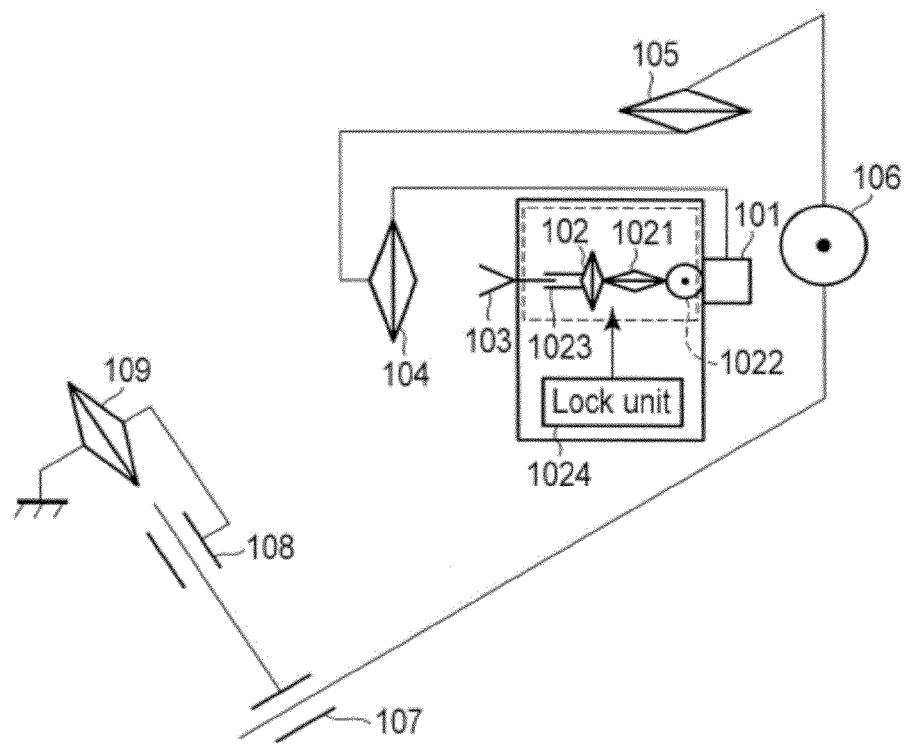
FIG. 15 is a schematic diagram showing the configuration of an example of an operation unit according to the second embodiment of the present invention.

Now, the second embodiment of the present invention is described. FIG. 15 is a schematic diagram showing the configuration of an operation unit 11 according to the second embodiment of the present invention. Here, components in FIG. 15 equivalent to those in FIG. 2 are provided with the same reference numbers as those in FIG. 2 and are not described below.

As shown in FIG. 15, in the second embodiment, joints 102, 1021, 1022, and 1023 as operable joints that can be independently operated are arranged in the vicinity of the grip portion 101. Each of these joints is adaptable to different degrees of freedom. In FIG. 15, joint 102 is a roll joint, joint 1021 is a yaw joint, joint 1022 is a pitch joint, and joint 1023 is a translation joint.

Furthermore, a lock unit 1024 is provided in the vicinity of joints 102, 1021, 1022, and 1023. The lock unit 1024 has an IC and a lock mechanism. The lock unit 1024 reads data indicating the joint structure of the distal end of a slave arm 31, and activates the lock mechanism so that the joints which are not adapted to the joint structure of the distal end of the slave arm 31 are inoperable among joints 102, 1021, 1022, and 1023. Here, the lock mechanism may be a mechanism that uses, for example, a latch member to mechanically lock the joint or may be a mechanism that uses, for example, a relay to electrically lock the joint. In addition, the output of an operation signal may be prevented even if the joint which is not adapted to the joint structure of the distal end is operated, or an operation signal from the joint which is not adapted to the joint structure of the distal end may be ignored.

Substantially the same configuration as that shown in FIG. 1 can be applied to the whole configuration of a master-slave manipulator as an example. However, in the second embodiment, a manipulator control unit 22 of a controller 20 is configured to communicate with a slave manipulator 30 to acquire data regarding the slave arm 31, and output the acquired data regarding the slave arm 31 to a master control unit 21. The lock unit 1024 is configured to be able to acquire, when needed, the data regarding the slave arm 31 stored in the master control unit 21. Here, the data regarding the slave arm 31 includes at least data regarding whether the slave arm 31 has a redundant joint at the distal end, and data regarding the structure of the joint when the slave arm 31 has a redundant joint at the distal end.

Figure 16:
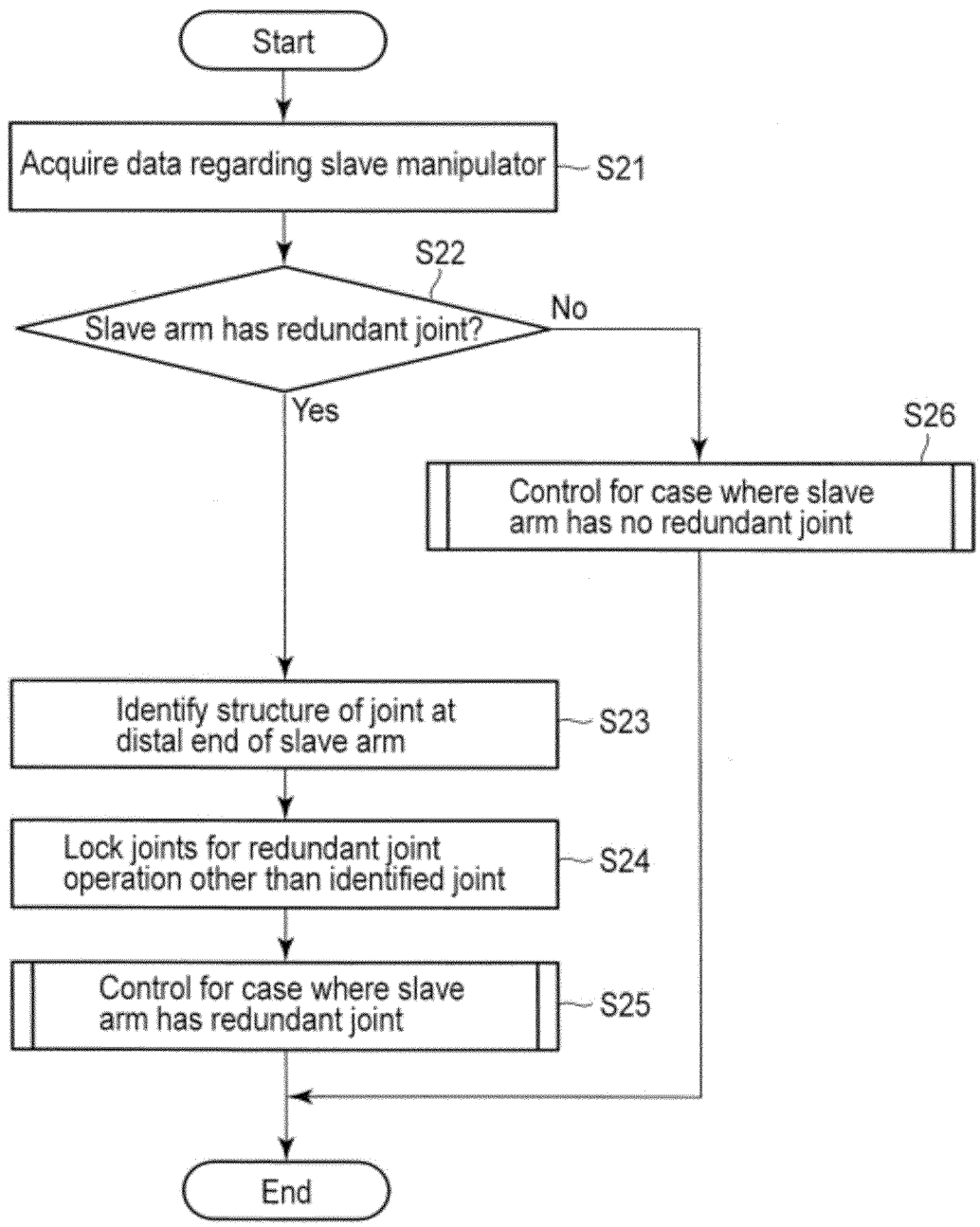
FIG. 16 is a flowchart illustrating the operation of a master-slave manipulator according to the second embodiment of the present invention.

FIG. 16 is a flowchart illustrating the operation of the lock unit 1024 in the master-slave manipulator according to the present embodiment.

At the start of the operation of the master-slave manipulator according to the present embodiment, the lock unit 1024 communicates with the master control unit 21 of the controller 20, and acquires the data regarding the slave arm 31 (step S21). After acquiring the data regarding the slave arm 31, the lock unit 1024 determines whether the slave arm 31 has a redundant joint at the distal end (step S22).

When determining in step S22 that the slave arm 31 has a redundant joint at the distal end, the lock unit 1024 identifies the structure of the joint at the distal end of the slave arm 31 in accordance with the data regarding the slave arm 31 (step S23). The lock unit 1024 then activates the lock mechanism so that the joints which are not adapted to the joint structure of the distal end of the slave arm 31 are inoperable among joints 102, 1021, 1022, and 1023 (step S24). For example, if the slave arm 31 has the structure shown in FIG. 3, the lock unit 1024 activates the lock mechanism so that joints 1021, 1022, and 1023 are inoperable. This is followed by the operation of the controller 20 of the master-slave manipulator shown in FIG. 6 in which the slave arm 31 has a redundant joint (step S25).

When determining in step S22, on the other hand, that the slave arm 31 has no redundant joint at the distal end, the lock unit 1024 does not activate the lock mechanism. This is followed by the operation of the controller 20 of the master-slave manipulator shown in FIG. 4 in which the slave arm 31 has no redundant joint (step S26).

As described above, in the present embodiment, the joints adapted to multiple degrees of freedom are connected as the operable joints for operating the joint at the distal end of the slave arm 31. The structure of the distal end of the slave arm 31 is then identified, and the joints of the operation unit 11 other than a necessary joint are made inoperable. Consequently, the technique described in the first embodiment can be applied to slave manipulators having various structures without changing the structure of the master operation input device 10.

Moreover, the joints other than a necessary joint are locked to be inoperable. Thus, there is no possibility that the operator may erroneously operate the joints other than the necessary joint and the slave arm 31 may behave incorrectly.

[Third Embodiment]

Figure 17:
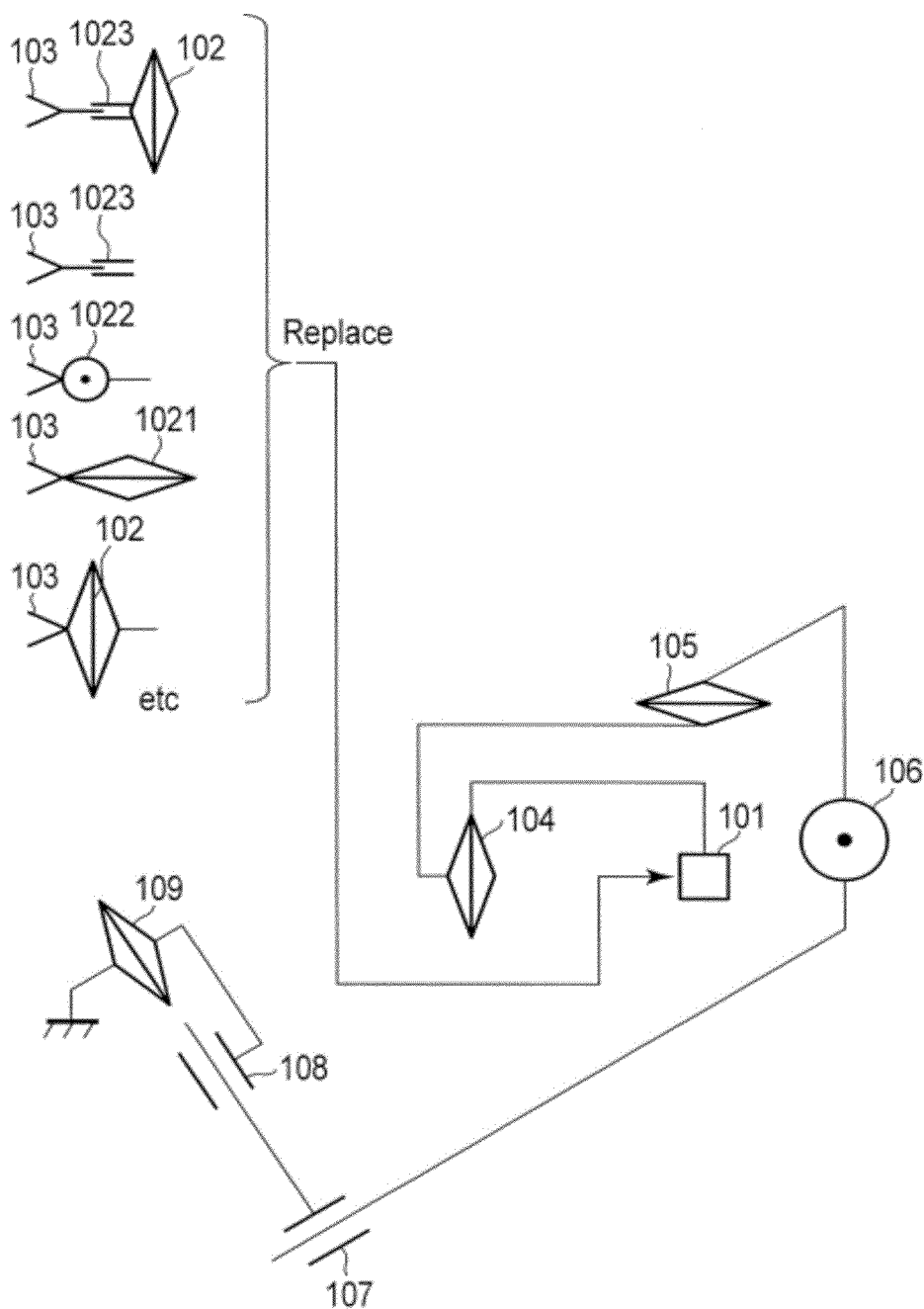
FIG. 17 is a schematic diagram showing the configuration of an example of an operation unit according to the third embodiment of the present invention.

Now, the third embodiment of the present invention is described. FIG. 17 is a schematic diagram showing the configuration of an operation unit 11 according to the third embodiment of the present invention. Here, components in FIG. 17 equivalent to those in FIG. 2 have the same reference numbers as those in FIG. 2 and are not described below.

As shown in FIG. 17, in the third embodiment, operable joints for operating a joint at the distal end of a slave arm 31 are replaceable. In FIG. 17, a joint 102, a joint 1021, a joint 1022, a joint 1023, and joints 102 and 1023 are shown as replaceable joints by way of example.

Substantially the same configuration as that shown in FIG. 1 can be applied to the whole configuration of a master-slave manipulator as an example. However, in the third embodiment, a manipulator control unit 22 of a controller 20 is configured to communicate with a slave manipulator 30 to acquire data regarding the slave arm 31, and output the acquired data regarding the slave arm 31 to a master control unit 21, as in the second embodiment. A master operation input device 10 is configured to be able to acquire, when needed, the data regarding the slave arm 31 stored in the master control unit 21.

FIG. 18 is a flowchart illustrating the operation of the master-slave manipulator according to the present embodiment.

At the start of the operation of the master-slave manipulator according to the present embodiment, the master operation input device 10 acquires the data regarding the slave arm 31 (step S31). After acquiring the data regarding the slave arm 31, the master operation input device 10 determines whether the slave arm 31 has a redundant joint at the distal end (step S32).

When determining in step S32 that the slave arm 31 has a redundant joint at the distal end, the master operation input device 10 identifies the structure of the joint at the distal end of the slave arm 31 in accordance with the data regarding the slave arm 31 (step S33). The master operation input device 10 then displays the identified data on a display unit 12. Looking at the data displayed on the display unit 12, the operator replaces the joint for redundant joint operation at the distal end located in the vicinity of the grip portion 101 with a joint adapted to the joint structure of the distal end of the slave arm 31 (step S34). This is followed by the operation of the controller 20 of the master-slave manipulator shown in FIG. 6 in which the slave arm 31 has a redundant joint (step S35).

When determining in step S32, on the other hand, that the slave arm 31 has no redundant joint at the distal end, there is no need for replacement. In this case, the operator attaches, to the grip portion 101, a joint having a given structure provided with the end effector operation unit 103. It should be understood that this joint need not be attached. This is followed by the operation of the controller 20 of the master-slave manipulator shown in FIG. 4 in which the slave arm 31 has no redundant joint (step S36).

As described above, in the present embodiment, the technique described in the first embodiment can be applied to slave manipulators having various structures without changing the structure of the master operation input device 10, as in the second embodiment.

Here, in the example described above, the operator replaces the operable joint for operating the redundant joint. This replacement may be automated.

While the embodiments of the present invention have been described above, the present embodiments have their advantageous effects particularly in a medical master-slave manipulator in which a surgical instrument is replaced during surgery and the joint structure of the slave manipulator 30 changes. Even if the joint configuration of the end effector of the slave manipulator 30 is modified during the master-slave operation, command values for the slave manipulator 30 can be modified by the control unit in real time during surgery as shown in FIG. 8.

While the present invention has been described above in connection with the embodiments, the present invention is not limited to the embodiments described above. It should be understood that various modifications and applications can be made within the spirit of the present invention. Furthermore, the embodiments described above include various stages of inventions, and various inventions can be extracted by properly combining the disclosed features. For example, when the above-mentioned problems can be solved and the above-mentioned advantages can be obtained even if some of all the features shown in the embodiments are eliminated, a configuration in which those features are eliminated can also be extracted as an invention.

What is claimed is:

1. A master-slave manipulator comprising:
   a slave manipulator comprising joints including multiple degrees of freedom;
   a master operation input device configured to allow an operator to uniquely input a position and an orientation, the master operation input device comprising:
      a first operation unit configured to output the position and orientation, and
      a second operation unit coupled to the first operation unit, the second operation unit comprising:
         an end effector operation unit; and
         a joint located between the first operation unit and the end effector operation unit,
      wherein the second operation unit is configured to output a value of the joint independently of the output of the first operation unit; and
   a control unit configured to:
      when the slave manipulator includes no redundant joint, calculate a first driving amount of each joint of the slave manipulator by using the position and orientation of the first operation unit and the value of the joint of the second operation unit as a position/orientation input command value for the end of the slave manipulator,
      generate a first joint driving command value based on the first driving amount, and
      control the slave manipulator in accordance with the first joint driving command value, and
   when the slave manipulator includes at least a redundant joint,
      calculate a second driving amount of each joint of the slave manipulator by hypothetically using the position and orientation from the first operation unit as a position/orientation input command value for the end of the slave manipulator including no redundant joint on the assumption that the distal end of the redundant joint is a fixed joint,
      generate a second joint driving command value including a driving amount of the joint of the second operation unit and the second driving amount, and
      control the slave manipulator in accordance with the second joint driving command value,
   wherein:
      the slave manipulator further comprises an interchangeable end effector, and
      the control unit determines whether the slave manipulator includes the redundant joint in accordance with the interchange of the end effector, and generates the first or second joint driving command value in accordance with the determination.

2. The master-slave manipulator according to claim 1, wherein the second operation unit and the redundant joint have the same structure.

3. The master-slave manipulator according to claim 1, wherein the second operation unit comprises:
   operable joints adapted to the multiple degrees of freedom of the slave manipulator and configured to be independently operable, and
   a lock unit configured to lock the operable joints that are not adapted to the redundant joint of the slave manipulator to keep these operable joints inoperable.

4. The master-slave manipulator according to claim 1, wherein the second operation unit is configured to be replaceable with a joint having the same structure as the redundant joint of the slave manipulator.

5. The master-slave manipulator according to claim 1, wherein the control unit determines whether the slave manipulator includes the redundant joint.

6. The master-slave manipulator according to claim 1, wherein the interchangeable end effector comprises a surgical instrument.

* * * * *